United States Patent [19]
Berson

[11] Patent Number: 6,073,039
[45] Date of Patent: Jun. 6, 2000

[54] DEVICE AND METHOD FOR REAL-TIME MONITORING OF AN ELECTROCARDIOGRAM DURING MAGNETIC RESONANCE IMAGING

[75] Inventor: Alan S. Berson, Rockville, Md.

[73] Assignee: The United States of America as represented by the Department of Health and Human Services, Washington, D.C.

[21] Appl. No.: 08/965,869

[22] Filed: Nov. 7, 1997

[51] Int. Cl.[7] .................................................. A61B 5/04
[52] U.S. Cl. ........................... 600/372; 600/544; 600/382
[58] Field of Search ................................. 600/372, 382, 600/383, 384, 386, 391, 393, 394, 509, 544, 546, 554

[56] References Cited

U.S. PATENT DOCUMENTS

| | | |
|---|---|---|
| 3,868,947 | 3/1975 | Holsinger . |
| 4,249,538 | 2/1981 | Musha et al . |
| 4,308,873 | 1/1982 | Maynard . |
| 4,763,075 | 8/1988 | Weigert . |
| 4,874,237 | 10/1989 | Cringle . |
| 4,887,609 | 12/1989 | Cole, Jr. . |
| 4,951,672 | 8/1990 | Buchwald et al. . |
| 4,991,580 | 2/1991 | Moore . |
| 5,038,785 | 8/1991 | Blakeley et al. . |
| 5,052,398 | 10/1991 | Gober . |
| 5,146,926 | 9/1992 | Cohen . |
| 5,209,233 | 5/1993 | Holland et al. . |
| 5,217,010 | 6/1993 | Tsitlik et al. . |
| 5,237,995 | 8/1993 | Cano . |
| 5,239,265 | 8/1993 | Sugahara . |
| 5,419,337 | 5/1995 | Dempsey et al. . |
| 5,436,564 | 7/1995 | Kreger et al. . |
| 5,891,136 | 4/1999 | McGee et al. ............................. 606/41 |

FOREIGN PATENT DOCUMENTS

| | | |
|---|---|---|
| 2-109545 | 4/1990 | Japan . |
| 3-244437 | 10/1991 | Japan . |
| 6-269426 | 9/1994 | Japan . |
| 7-222726 | 8/1995 | Japan . |
| WO 92/07509 | 5/1992 | WIPO . |
| WO 92/17112 | 10/1992 | WIPO . |

*Primary Examiner*—Linda C. M. Dvorak
*Assistant Examiner*—Roy Gibson
*Attorney, Agent, or Firm*—Merchant & Gould P.C.

[57] ABSTRACT

An electrode assembly for monitoring bioelectric signals includes a first electrode member and a second electrode member disposed around the first electrode member. When the electrode assembly is placed on a body of a person, a bioelectric signal is monitored by measuring the electrical potential between the first and second electrode members with the measurement device. The first and second electrode members may be single electrodes or two or more electrodes connected by conductors. Alternatively, the first and second electrodes can be formed from an array of electrodes by connecting the electrodes in a desired configuration either electrically or by use of a software algorithm.

30 Claims, 9 Drawing Sheets

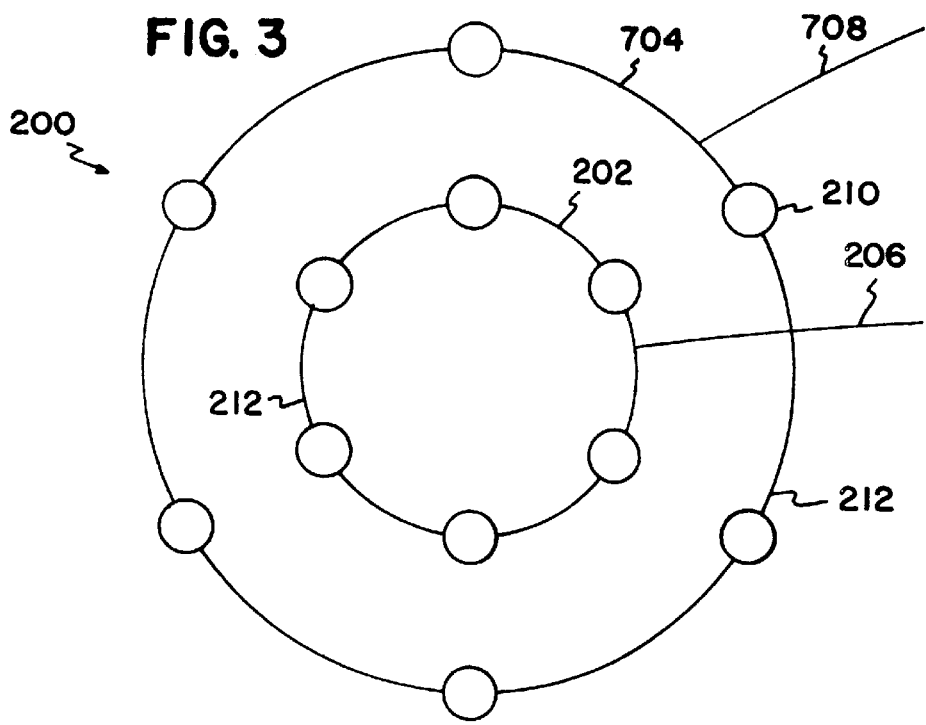
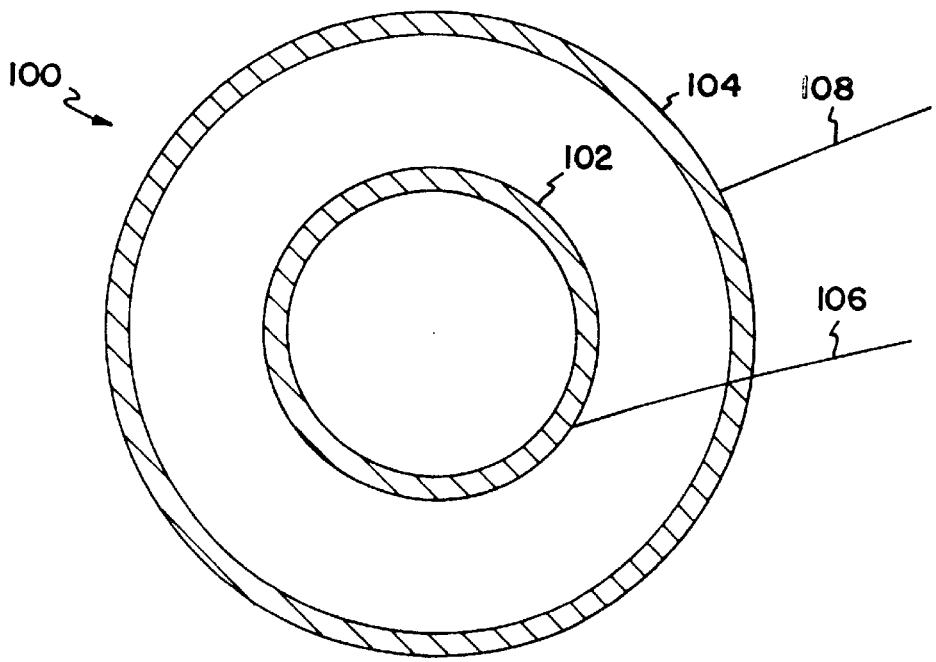

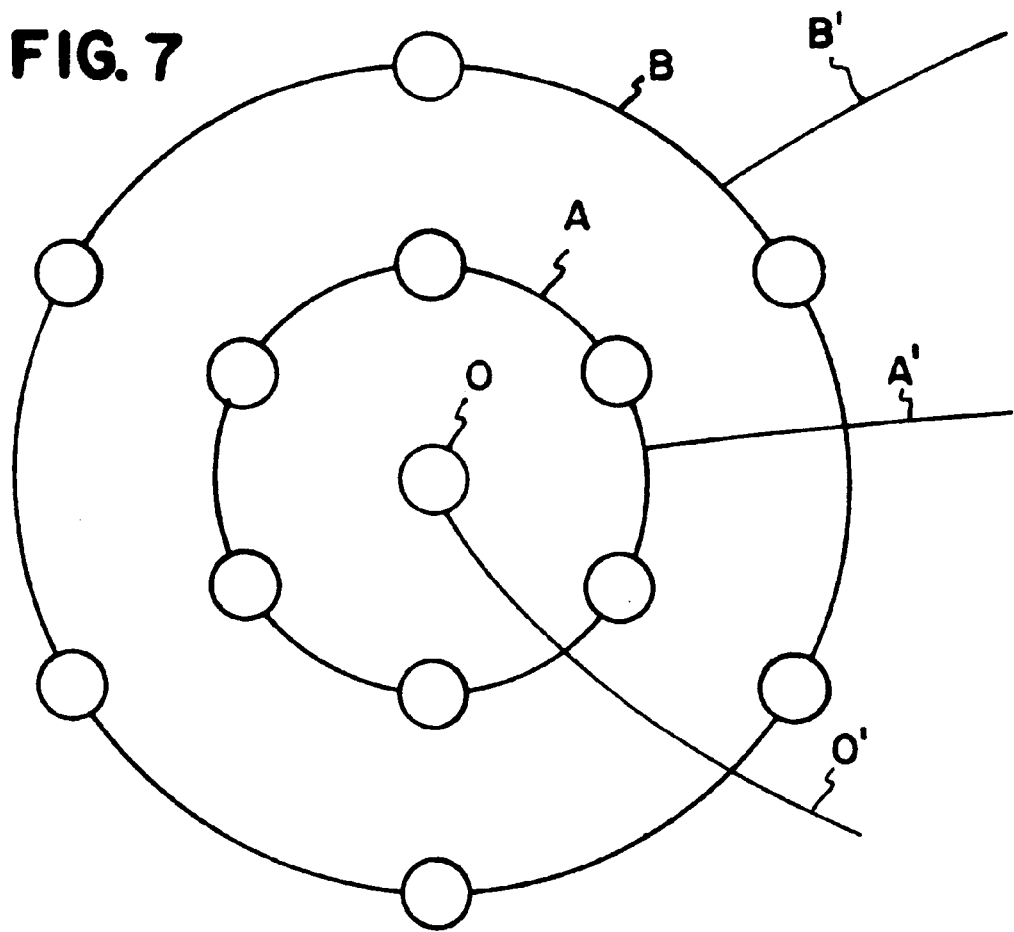

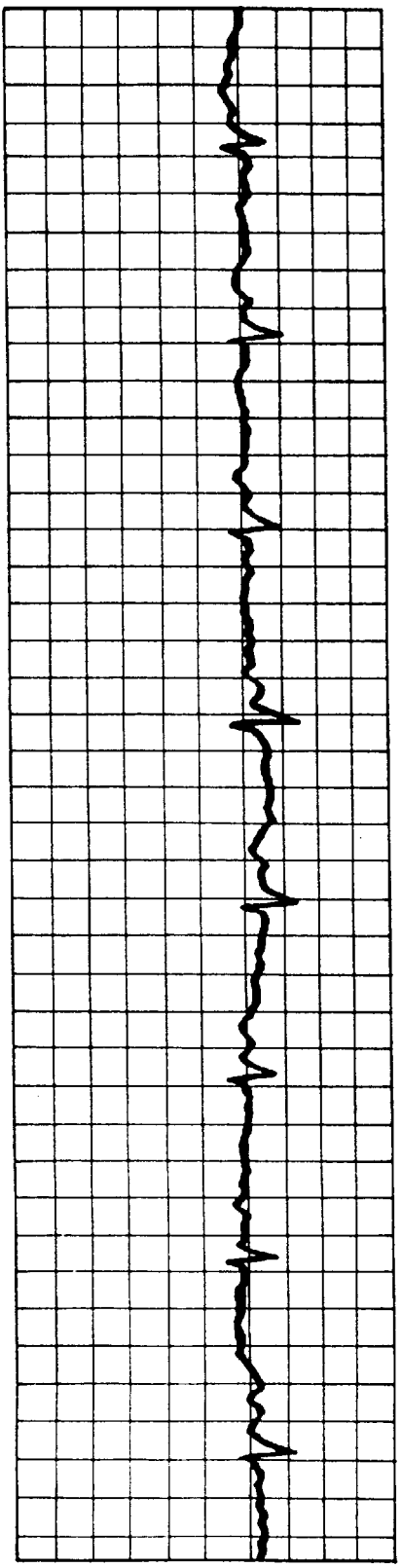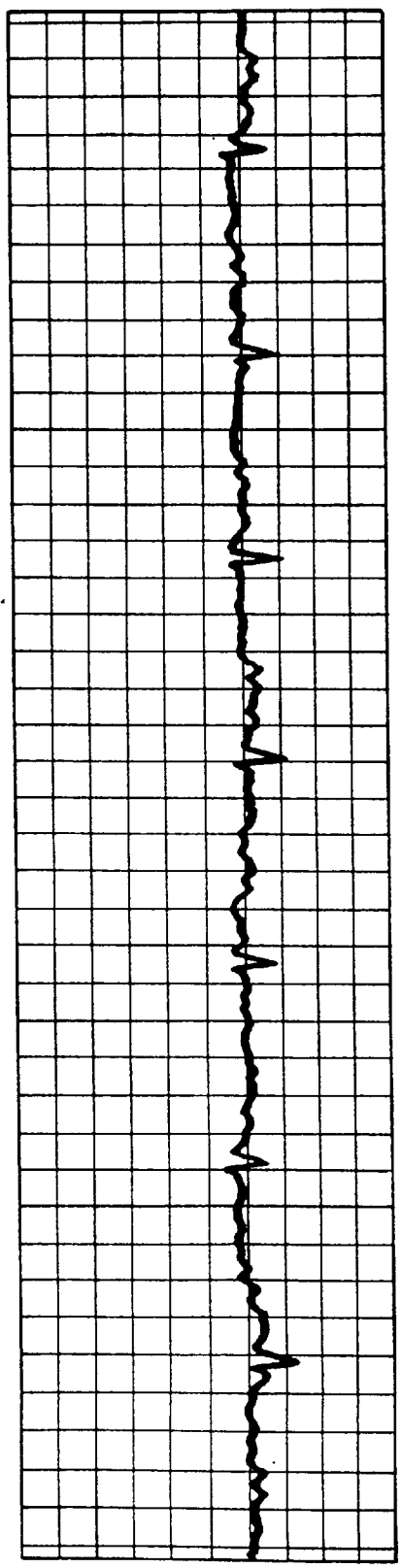

DEVICE AND METHOD FOR REAL-TIME MONITORING OF AN ELECTROCARDIOGRAM DURING MAGNETIC RESONANCE IMAGING

FIELD OF THE INVENTION

The present invention is, in general, directed to an electrode array for monitoring bioelectric signals. In particular, the present invention relates to an electrode array having two electrode members, one inside of the other, which can be used to monitor the electrocardiogram of a patient during a magnetic resonance imaging (MRI) procedure.

BACKGROUND OF THE INVENTION

Cardiac and cardiovascular imaging using magnetic resonance imaging (MRI) techniques is of intense interest. The use of MRI has obvious advantages over other imaging techniques which typically employ radiation, such as X-rays. However, for cardiac studies, the subject is often required to remain within the MRI magnet for at least thirty to sixty minutes. During this period, it is advisable to observe the electrocardiogram (ECG) of the patient continuously, especially if imaging is being used to diagnose or study potential cardiac conditions. Moreover, many imaging protocols include stressing the cardiac system by, for example, pharmacological methods, to view the heart or other portions of the system under stress. Again, it is advisable to monitor the heart under these conditions to improve the diagnosis and to improve the safety of the imaging techniques (e.g., to indicate if the stressing of the cardiac system is causing potentially dangerous or damaging results.)

The electrocardiogram typically is presented in the form of a potential difference between two electrodes measured as a function of time. The potential difference arises from the electrical signals generated by the heart during its cardiac cycle. The heart's electrical discharge spreads through the conducting tissues of the body to the body surface where it can be monitored using the electrodes. A typical cardiac cycle is presented in FIG. 1. The QRS portion of the cardiac electrical signal represents ventricular depolarization of heart cells, which causes the ventricles to contract. The ST portion of the ECG corresponds to the repolarization or resetting of the electrical system after the contraction. By observation of the form and amplitudes of these and other portions of the ECG, various cardiac conditions can be diagnosed.

The monitoring of the ECG during MRI procedures is complicated by the presence of the magnet and its associated high intensity magnetic field, as well as the gradient fields and rf sampling fields used in MRI techniques. Furthermore, during an MRI procedure, the blood of the patient become magnetically polarized due to the magnet and rf fields. The blood acts as a moving conductor and generates magnetohydrodynamic potentials as the blood flows through the body. Moreover, these potentials are constantly changing as the velocity of the blood flow changes over the course of the cardiac cycle (i.e., the velocity of the blood increases as it is pumped and then slows over time until it is pumped again).

The potentials generated by the blood flow disrupt, distort, and/or overwhelm the cardiac signals as received by the ECG electrodes. This greatly reduces the diagnostic quality of the ECG signals. While attempts have been made to reduce the direct interference of the rf and gradient fields by, for example, shielding, filtering and/or monitoring of the ECG only during quiescent periods, there has not been a satisfactory method or device for addressing the effect on the ECG of the magnetohydrodynamic potentials arising from the flow of blood.

SUMMARY OF THE INVENTION

Generally, the present invention relates to a method and a device for monitoring bioelectric signals, even during magnetic resonance imaging. One embodiment is an electrode assembly for monitoring bioelectric signals. The electrode assembly includes a first electrode member, a second electrode member disposed around the first electrode member, a first lead electrically connected to the first electrode member, and a second lead electrically connected to the second electrode member. The first and second leads are adapted for coupling to a measurement device. When the electrode assembly is placed on a body of a person, a bioelectric signal is monitored by measuring the electrical potential between the first and second electrode members with the measurement device.

Another embodiment is a device for monitoring bioelectric signals. The device includes a number of electrodes arranged in an array with conductors connecting individual electrodes. Two or more leads are coupled either to one of the electrodes or one of the conductors. The leads are adapted for coupling to a measurement device. A mechanism is operatively connected to the electrodes to define two or more electrode members. Each of the electrode members includes two or more electrodes and one of the electrode members is positioned around the other electrode member. Each of the electrode members is electrically coupled to at least one of the leads. When the electrode array is placed on a body of a person, a bioelectric signal is monitored by measuring the electrical potential between the leads coupled to the two electrode members.

A further embodiment is a method for monitoring bioelectric signals. The method includes positioning an electrode assembly on a body of a person. The electrode assembly has a first electrode member and a second electrode member with the second electrode member positioned around the first electrode member. After the electrode assembly is placed on the body of the person, the potential between the first and second electrode members is measured to monitor the bioelectric signal.

Still another embodiment is a method for monitoring bioelectric signals. The method includes, first, positioning an array of electrodes on a body of a patient. The array of electrodes includes a number of electrodes forming the array and conductors connecting individual electrodes. Two or more leads are coupled either to one of the electrode or one of the conductors. A mechanism is operatively connected to the electrodes to define a pair of electrode members. After the array of electrodes is positioned, a series of pairs of electrode members is sequentially defined using the mechanism. Each electrode member includes two or more electrodes. One of the electrode members is disposed around the other electrode member and each of the electrode members is electrically coupled to one of the leads. Next, a quality characteristic of the bioelectric signal is determined for each pair of electrode members in the series. One of the pairs is then chosen based on the quality characteristic and the bioelectric signal is monitored with the array configured as the chosen one of the pairs of electrode members. The bioelectric signal is measured as the potential between the leads attached to the electrode members.

The above summary of the present invention is not intended to describe each disclosed embodiment or every implementation of the present invention. The Figures and the detailed description which follow more particularly exemplify these embodiments.

BRIEF DESCRIPTION OF THE DRAWINGS

The invention may be more completely understood in consideration of the following detailed description of various embodiments of the invention in connection with the accompanying drawings, in which:

FIG. 2 is a diagrammatic representation of one embodiment of an electrode assembly for monitoring bioelectric signals during MRI scanning according to the invention;

FIG. 3 is a diagrammatic representation of another embodiment of an electrode assembly for monitoring bioelectric signals during MRI scanning according to the invention;

FIG. 7 is a diagrammatic representation of an electrode assembly made according to the invention that was used in the experiments described below;

FIGS. 8c and 8d are electrocardiograms obtained using the electrode assembly of FIG. 7 centered on the left mid-axiallary line, fifth intercostal space, of another subject outside (8c) and inside (8d) a 1.5 T MRI magnet;

Figure 1:
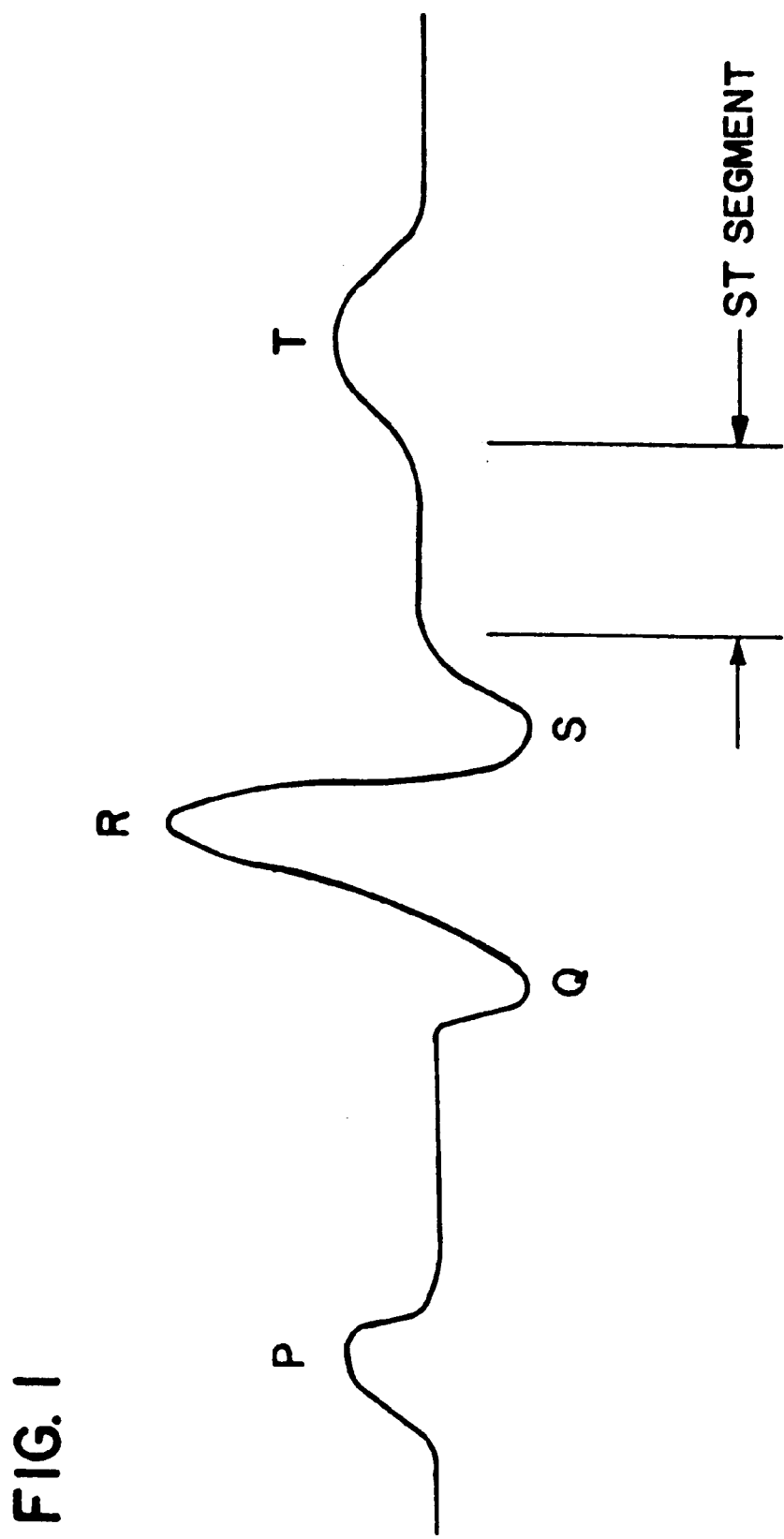
FIG. 1 is an example of an electrocardiogram signal.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION OF THE PREFERRED EMBODIMENT

The present invention is believed to be applicable to the monitoring of bioelectric signals including the electrocardiogram. In particular, the present invention is directed to a method and device for monitoring bioelectric signals even during magnetic resonance imaging procedures. While the present invention is not so limited, an appreciation of various aspects of the invention will be gained through a discussion of the examples provided below.

Referring to FIG. 2, an electrode assembly 100 for monitoring bioelectric signals, such as an electrocardiogram (ECG), includes an inner electrode member 102 and an outer electrode member 104. The outer electrode member 104 is typically formed so as to surround the inner electrode member 102. Leads 106 and 108 for coupling to external electronics (not shown), such as a measurement device, are attached to each of the electrode members 102 and 104.

The measurement device (not shown) may be used to observe bioelectric signals, such as the ECG. For example, the measurement device may be a potentiometer that is capable of observing the potential difference between the two electrode members 102 and 104 over time. In some embodiments, the potential difference is determined by attaching the leads 106 and 108 to different inputs of a differential amplifier, the output of the differential amplifier providing the potential difference. Other suitable external electronics and measuring devices for determining the potential difference, or other electrical properties, such as current amplitude, between the two electrode members 102 and 104 are known and may be used. The external electronics also may include components, such as filters or shielding, to remove or prevent interference due to the MRI magnet and/or the gradient and rf fields used during the MRI procedure. The leads 106 and 108 may also be shielded to reduce interference.

The shape of the electrodes members 102 and 104 is relatively unimportant. The electrode assembly 100 in FIG. 2 has two ring-like electrode members 102 and 104, however, other regular shapes, including squares, rectangles, triangles, as well as irregular shapes, may be used. Preferably, the inner electrode member 102 has the same shape, in a smaller size, as the outer electrode member 104, although this is not necessary for the operation of the invention.

The electrode members 102 and 104 may each be formed as a single electrode, as illustrated in FIG. 2. In other embodiments, the electrode members may be formed using two or more individual electrodes which are connected together by conductors. One such embodiment is illustrated in FIG. 3 in which the electrode assembly 200 has two electrode members 202 and 204 that are each formed from two or more electrodes 210 (in the configuration illustrated in FIG. 3 there are six electrodes per electrode member) arranged in the desired shape and connected together by conductors 212. A single lead 206 and 208 is attached to each electrode member 202 and 204 for connection to the external electronics (not shown).

The two or more electrodes 210 that are used to form the electrode members 202 and 204 approximate the situation where the electrode members are single electrodes in the appropriate shape. This approximation is typically improved by the use of larger numbers of electrodes (e.g., using six instead of three electrodes) or electrodes in a form resembling at least a part of the electrode member (e.g., using two hemispherical electrodes to form a circular electrode member). Often, the two or more electrodes 210 are placed at regular intervals around the shape of the electrode member 202 and 204. However, this is not necessary. The same number of electrodes is preferably used for both of the electrode members 202 and 204, but again this is not necessary. In addition, the electrodes 210 of the two electrode members 202 and 204 are preferably situated at the same relative points along the shape of the respective electrode members.

The electrode members 102, 104, 202, and 204 may be formed using a variety of different types of electrodes including many of those currently used in conventional bioelectric signal monitoring devices. Typically, however, the amount of magnetic material in the electrode members is minimized to avoid interactions with the MRI magnet. Suitable electrodes can be made from silver/silver chloride, stainless steel, and German silver. Silver/silver chloride electrodes are preferred because of their excellent polarization properties. Many commercially available ECG electrodes are of the silver/silver chloride variety. Often, the ECG electrode are coated with an adhesive for adhering the electrode to the skin of the patient. The ECG electrodes are also often coated with a conducting gel to ensure adequate conduction between the patient and the electrodes. Suitable commercially available, adhesive-backed, pre-gelled silver/silver chloride ECG electrodes are available, for example, from Quinton Instrument Company (catalog number 000204-001) or Becton-Dickinson.

Although no theory is essential to the invention, it is believed that the formation of the electrode assembly with an inner and an outer electrode member facilitates the monitoring of bioelectric signals because the magnetohydrodynamic signals generated by the flow of blood are canceled and/or averaged by the assembly. It is believed that the potential generated by blood flow near the outer electrode is approximately equal to the potential generated by blood flow near the inner electrode. Thus, when a potential difference is determined, these two potentials cancel each other.

To facilitate the proper functioning of the assembly, it may be necessary to relocate the assembly at different points on the body of the patient to find a position from which a relatively distortion- or interference-free bioelectric signal can be obtained. This position may correspond to a portion of the body where th blood flow near each of the electrodes is relatively equal. More precisely, however, because the potential caused by blood flow depends on the distance between the flowing blood and the electrodes (the potential at any given point is proportional to the inverse of the square of the distance between the point and the field source), as well as the orientation of the blood flow, the optimal position of the electrodes will be a somewhat more complex function of the amount, velocity, orientation, and spatial positioning of blood flow with respect to the electrodes. It has been determined, however, that at least for some individuals, the placement of an electrode assembly with two circular electrode members having diameters of 3 and 6 cm, respectively, at a position which is centered on the sternum at the fifth intercostal space can provide a reasonably noise-free ECG. This may vary between individuals.

Another consideration in forming the electrode assembly 100 and 200 is the appropriate spacing between the inner and outer electrode members 102, 104, 202, and 204. The two electrodes typically are spaced-apart so that as the electrical signal from the heart spreads through the body, there is sufficient time to develop a potential difference between the electrodes. This principle is well-known by those who measure electrocardiograms by conventional techniques, which typically use disc-shaped electrodes. However, from the point of view of interference caused by the hydrodynamic effect, it may be detrimental if the two electrode members 102 and 104 are separated by too much space, since the blood flow patterns through the regions adjacent to the electrode members 102 and 104 will likely vary considerably with increased separation. Typically, the distance between the inner and outer electrodes is to 5 cm, preferably 2 to 4 cm, and more preferably 2.5 to 3.5 cm.

A bioelectric signal obtained from this electrode assembly may be used for a variety of diagnostic purposes. For example, an ECG obtained in this manner may be used to determine heart irregularities and/or allow for the observation of the heart under stress (typically induced pharmacologically). In addition, the ECG may be useful for timing the acquisition of the image from the MRI apparatus. For example, a processor (not shown) may be provided which receives the ECG and directs the MRI apparatus in the timing of the pulses sequences used to obtain the image. For example, the processor may direct the MRI apparatus to initiate a sequence when a particular portion of the ECG has been received or at a predetermined time after that portion of the ECG. This can be used to provide a reliable method for imaging the heart at particular positions in the cardiac cycle.

Another embodiment of the invention is the use of two electrode assemblies which are placed on different portions of the body of the patient. These two electrode assemblies are positioned so that the vectors from the heart to each of the electrode assemblies are approximately orthogonal. For example, one electrode assembly may be positioned on the front upper thorax of the patient and the second electrode assembly may be positioned on the left sagittal thorax of the patient. In this configuration, the electrode assemblies can be used to monitor the heart during the cardiac cycle. The electrical signals in the heart can be represented approximately as an electrical dipole. The orientation of the dipole moves throughout the cardiac cycle. By positioning two electrode assemblies, as described above, the change in orientation of the dipole can be monitored throughout the cardiac cycle.

Figure 4:
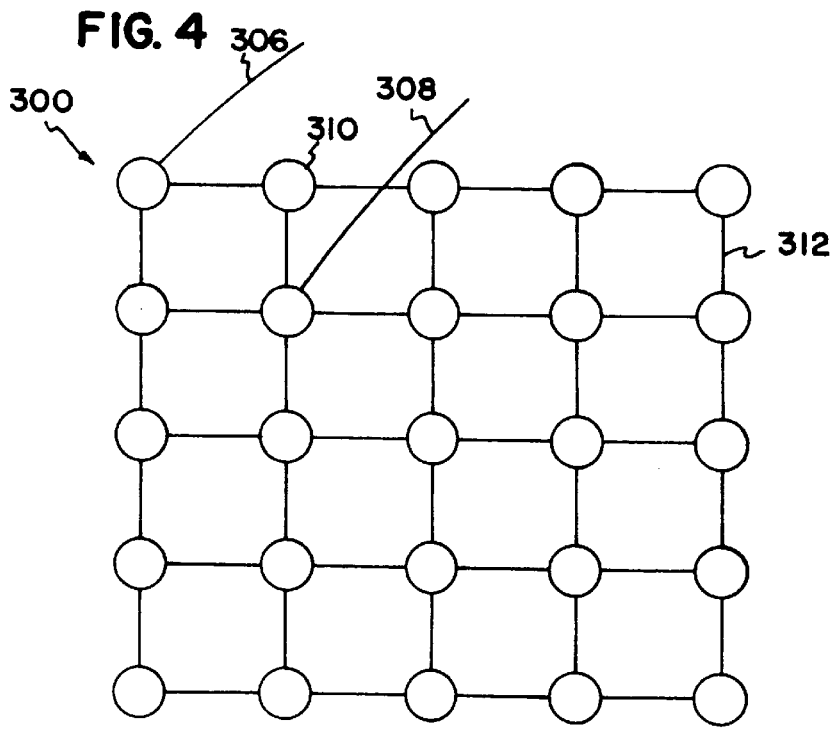
FIG. 4 is a diagrammatic representation of one embodiment of an electrode assembly from which two or more electrode members can be formed for monitoring bioelectric signals during MRI scanning according to the invention.
Figure 5A:
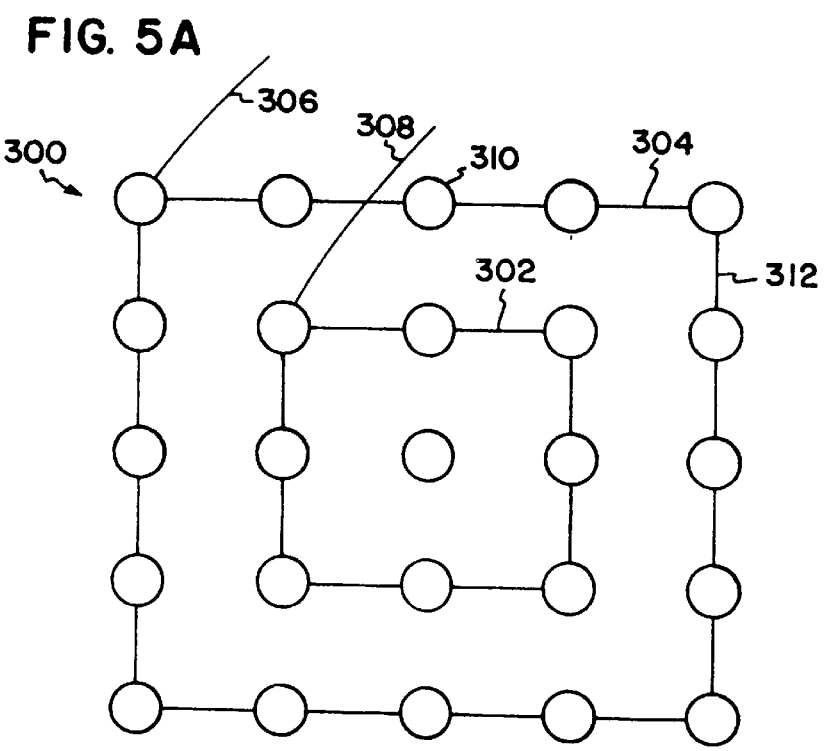
FIGS. 5a and 5b are diagrammatic representations of the electrode array of FIG. 4 showing possible electrode member configurations.
Figure 5B:
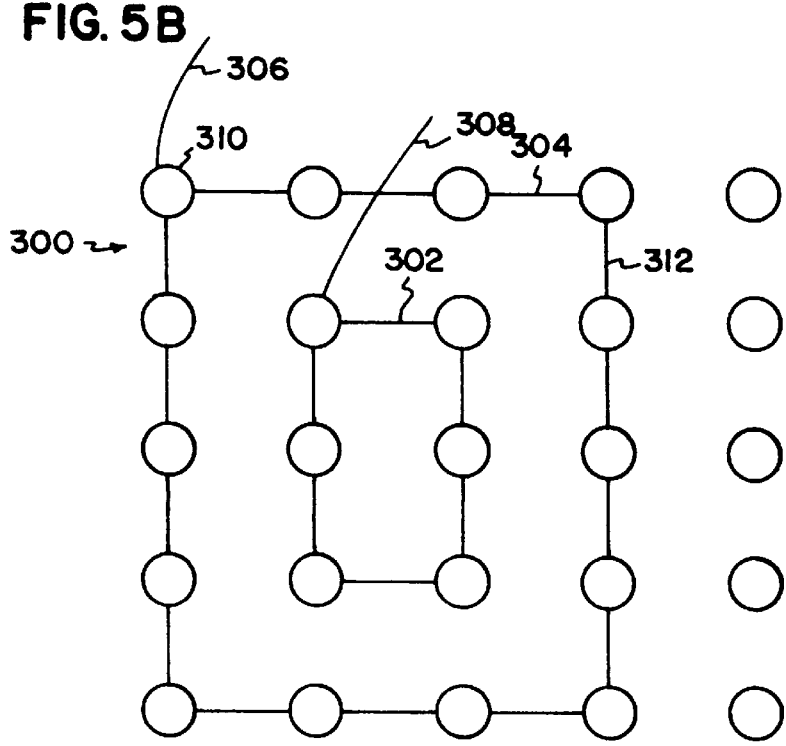

As described above, it may be necessary to move the electrode members to find a position on a patient from which a satisfactory bioelectric signal can be measured. In some embodiments of the invention, this situation is resolved by providing, an array 300 of electrodes 310, as illustrated in FIG. 4, which are coupled together by conductors 312 such that groups of the electrodes can be chosen, either by hardware or software manipulation, to form pairs of electrode members. Examples of pairs of electrode members are shown in FIGS. 5a and 5b, in which only the conductors connecting the electrode pairs are indicated.

Figure 6:
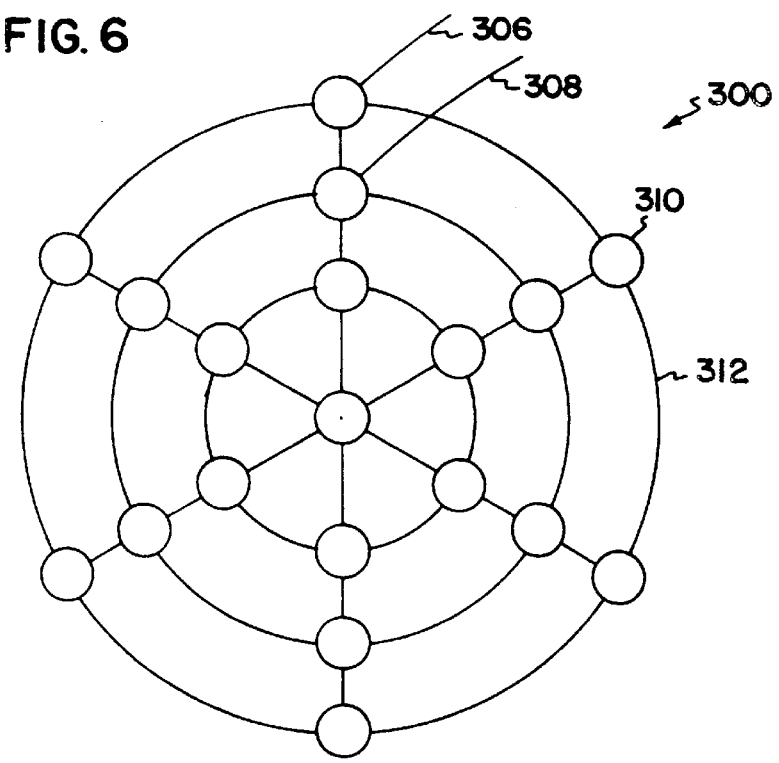
FIG. 6 is a diagrammatic representation of another embodiment of an electrode array from which two or more electrode members can be formed for monitoring bioelectric signals during MRI scanning according to the invention.

The array 300 of electrodes 310 can be formed using any number of electrodes. The electrodes 310 may be formed in rows and columns as illustrated in FIG. 4 or as a series of concentric rings as illustrated in FIG. 6. Other array configurations may also be designed and used, including both regularly spaced arrays and random arrays.

The conductors 312 typically couple neighboring electrodes, although in some embodiments, the conductors 312 may couple electrodes that are distantly spaced. Suitable conductors 312 include, for example, wires, metal strips, or layers of a conductive material deposited on a substrate (e.g., copper connecting lines on a circuit board). In one embodiment, a switching mechanism (not shown) is provided to control which conductors 312 are active (i.e., which conductors are used to couple electrodes 310 to form the pair of electrode members 302 and 304, or in other words, through which conductors the current flows). The switching mechanism may be directly connected to the electrodes 310 or the conductors 312. Non-limiting examples of suitable switching mechanisms include: (1) a switching mechanism that, when activated, creates a connection between the electrodes 310 and the desired conductor(s) 312, leaving the rest of the conductors adjacent to the electrodes electrically isolated or (2) a switching mechanism that interrupts the conductors 312 and separates the conductors into at least two pieces; when the conductor 312 is active, the switching mechanism connects the ends of the conductor 312 using a conductive material so that current can flow and when the conductor 312 is not needed to form the electrode member, the switching member deactivates the conductor 312 and removes the conductive material and, optionally, replaces it with an insulating material, to prevent the flow of current. It will be appreciated that a variety of other switching mechanisms can be provided.

In some embodiments, the switching mechanism is activated manually, allowing a user to choose and/or design the configuration of the pair of electrode members manually. In other embodiments, the electrode array 300 is coupled to a processor (not shown), which may be used to control the switching mechanism. The processor may include an input device that allows a user to designate a desired electrode array configuration. Alternatively, the processor may be programmed with a number of electrode member configurations or the processor may include an algorithm that determines possible configurations. In either case, the user may have an option to accept or reject each configuration for testing. This testing is accomplished by observing the electrocardiogram, preferably in the presence of the MRI apparatus and more preferably under the conditions of the MRI procedure. The user and/or the processor may determine whether the bioelectric signal obtained using this particular pair of electrode members is adequate. By adequacy, it is meant that the information that is sought from a particular test is sufficient for the purposes that the electrocardiogram is being observed (e.g., monitoring or diagnosis).

In another embodiment, a software mechanism is implemented for defining the pair of electrode members 302 and 304. The software mechanism obtains readings of the potential for each electrode 310 in the array 300 relative to a reference electrode (not shown). The software mechanism then forms pairs of electrode members 302 and 304, such as those shown in FIGS. 5A and 5B, within a processor (not shown) and combines the potential for two or more electrodes 310 which make up each of the electrode members 302 and 304. In this embodiment, there is no need to physically connect or disconnect electrodes 310 as this is all done in the software mechanism.

In some embodiments, the process of determining adequate pairs of electrode members is automated. The processor includes an algorithm for forming pairs of electrode members 302 and 304 from the array 300 of electrodes 310 using either the hardware switching mechanism or the software mechanism described above. This algorithm may include a portion which seeks to improve the electrode members by making minor alterations in electrode member configuration. The processor also includes a testing algorithm which determines the accuracy of the bioelectric signals received by each pair of electrode members. Typically, the testing algorithm compares one or more quality characteristics of the bioelectric signals to determine the suitability of each pair of electrode members. Examples of suitable quality characteristics include the amplitude and/or shape of a portion of the bioelectric signal and the signal-to-noise ratio. In some embodiments, the bioelectric signal may be compared to a bioelectric signal taken when the patient is not in the MRI magnet. Accuracy can be measured as the difference between the signals. Other quality characteristics may also be used. An ECG recorded outside the MRI system may be used as a comparative reference to determine the best quality characteristics.

The processor may stop testing pairs of the electrode members when a suitable pair has been found. Alternatively, the processor may test a large number of electrode members and then select, or permit a user to select, an electrode pair that provides the most accurate and distortion/interference-free signal. The described automation sequence can be used for a quick determination of a suitable electrode member configuration to obtain accurate bioelectric signal measurements.

Leads 306 and 308 are provided with the electrode array 300 to connect the electrode members 302 and 304 to external electronics (not shown), such as a measurement device. A variety of lead configurations can be use. For example, leads 306 and 308 may be provided which are connected to two of the electrodes 310 or two of the conductors 312. In this case, the particular electrodes 310 or conductors 312 attached to the leads must be included in the electrode configuration of the pair of electrode members 302 and 304. Alternatively, leads 306 and 308 may be connected to each of the electrodes.

An alternative lead configuration includes leads coupled to more than two of the electrodes 310 or conductors 312. In this case, the electrode members 302 and 304 must each include at least one electrode 310 or conductor 312 which is coupled to a lead. If the electrode member has more than one electrode or conductor that is coupled to a lead, only one of the leads needs to be chosen for connection to the external electronics. The other leads may be left floating or, alternatively, a switching mechanism may be provided that electrically couples one of the leads to each electrode member and electrically isolates the other leads. This may be particularly useful when a hardware switching mechanism is used.

EXAMPLE

An electrode assembly according to the invention was prepared as Illustrated in FIG. 7. The electrode array had a central electrode ("O"), an inner ring ("A") of six electrodes coupled by conductors, and an outer ring ("B") of six electrodes coupled by conductors. Leads (O', A', and B') were coupled to each of these structures. The inner ring had a diameter of 3 cm and the outer ring had a diameter of 6 cm. The electrodes were adhesive-backed, pre-gelled electrodes from Quinton Instrument Company (catalog number 000204-001). The electrodes were 12 mm in diameter and were applied using standard ECG techniques, in which the skin of the patient was rubbed with alcohol prior to application of the electrode. The conductors were conventional conducting wires The leads were connected to a differential amplifier constructed from commercially available integrated circuits and other resistor and capacitor components.

Figure 8A:
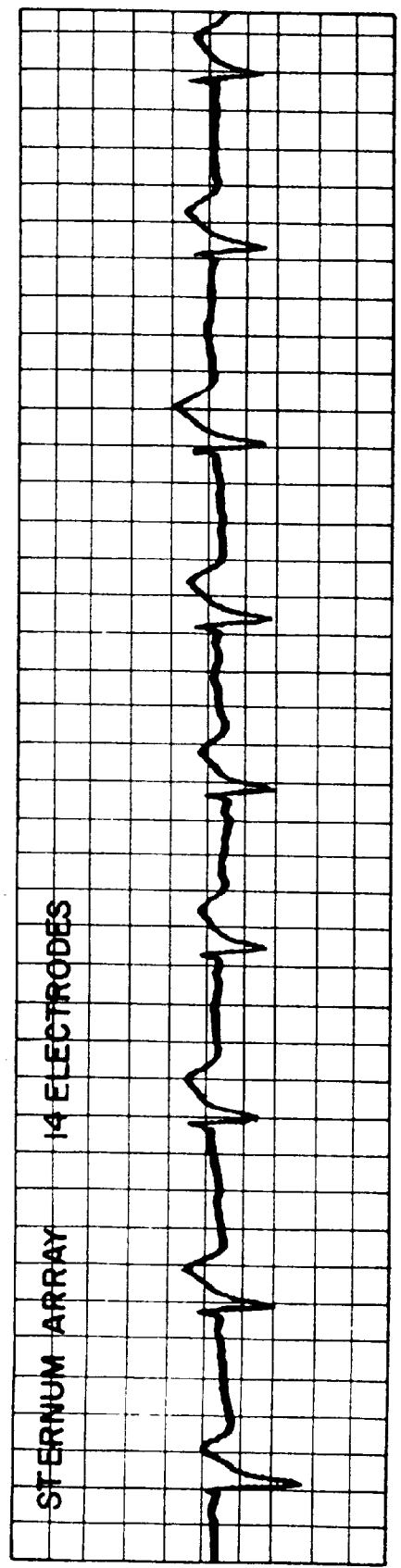
FIGS. 8a and 8b are electrocardiograms obtained using the electrode assembly of FIG. 7 centered on the sternum, fifth intercostal space, of a subject outside (8a) and inside (8b) a 0.5 T MRI magnet.
Figure 8B:
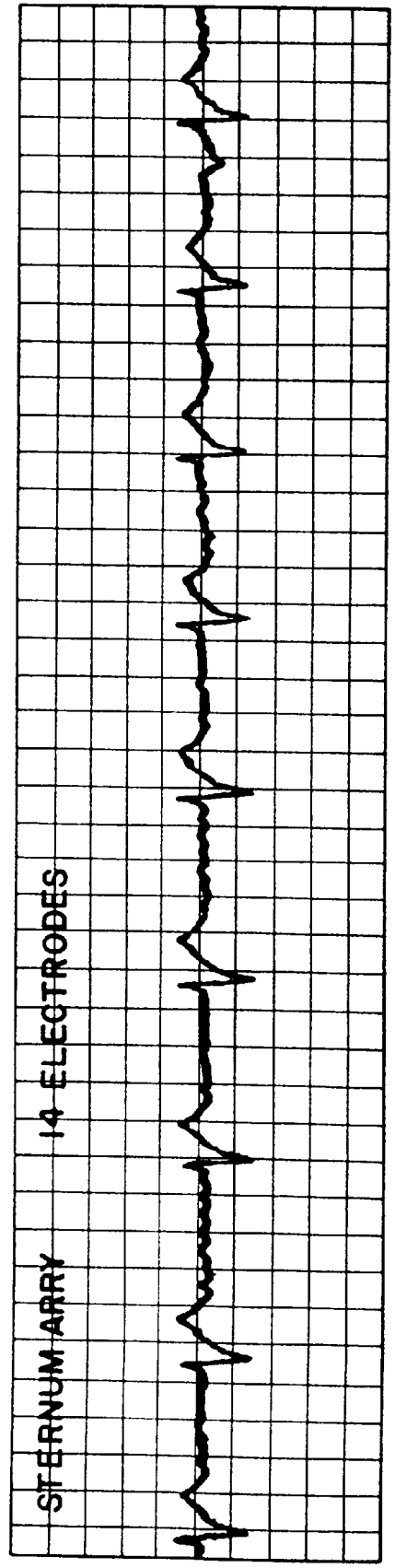

The electrode assembly was positioned at the fifth intercostal space on the sternum of an individual. FIG. 8a is an electrocardiogram taken outside of the MRI magnet showing the potential difference over time between electrode members "A" and "B" of the electrode assembly of FIG. 7. This is a typical electrocardiogram signal. FIG. 8b shows the electrocardiogram for the same individual and the same electrode configuration, but this time the individual is inside a 0.5 T MRI magnet. FIGS. 8c and 8d show electrocardiograms outside and inside a 1.5 T magnet. In this case, the electrode array was positioned on the left mid-axiallary line at the level of the fifth intercostal space. By comparing FIGS. 8a and 8b as well as 8c and 8d, it is apparent that the electrode configuration of FIG. 7 eliminates distortion and interference due to the MRI magnet. The resulting electrocardiogram could be used for diagnosing of cardiac conditions, and especially ST electrode changes.

The potential differences between "O" and "A", as well as between "O" and "B", were also observed to determine if a suitable electrocardiogram could be obtained by using a single central electrode within a larger ring electrode. The resulting electrocardiograms were distorted and could not be used for diagnostic purposes.

Figure 9A:
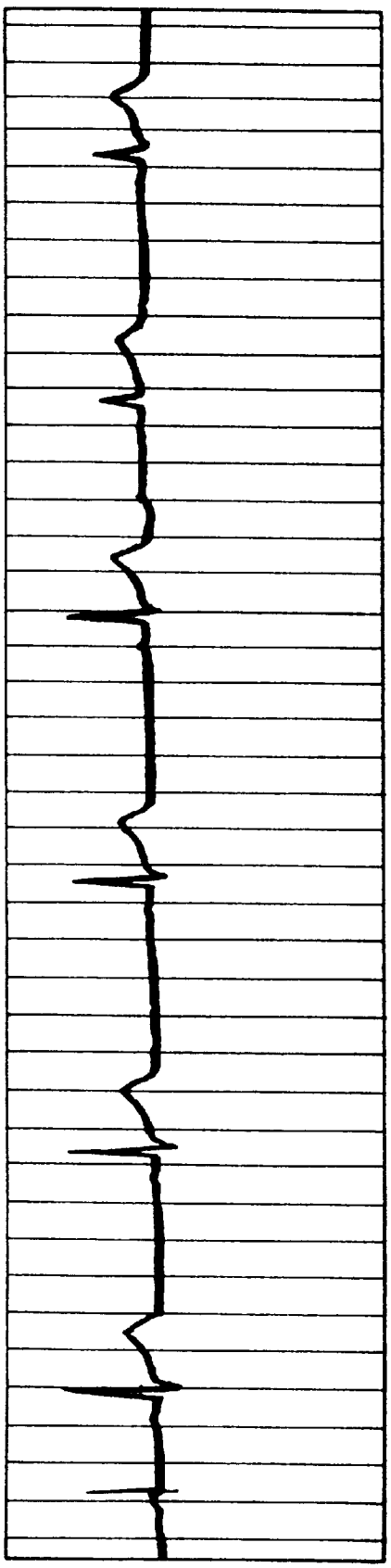
FIGS. 9a and 9b are electrocardiograms obtained from a subject using a conventional electrode array outside (9a) and inside (9b) a 0.5 T MRI magnet.
Figure 9B:
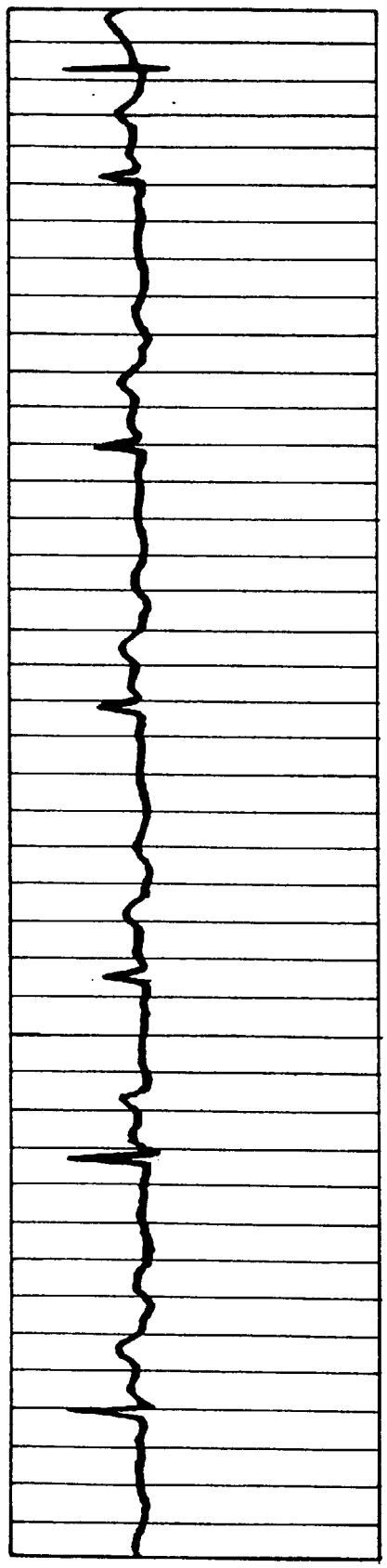
Figure 9C:
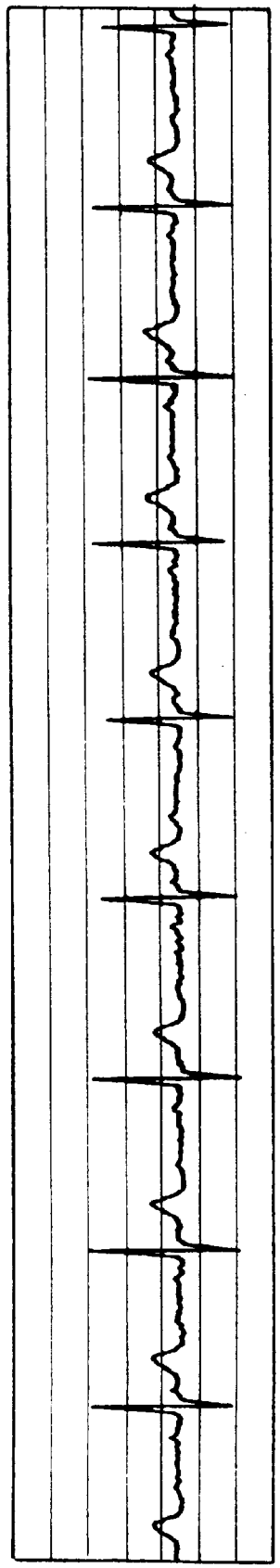
FIGS. 9c and 9d are electrocardiograms obtained from another subject using a conventional electrode array outside (9c) and inside (9d) a 1.5 T MRI magnet.
Figure 9D:
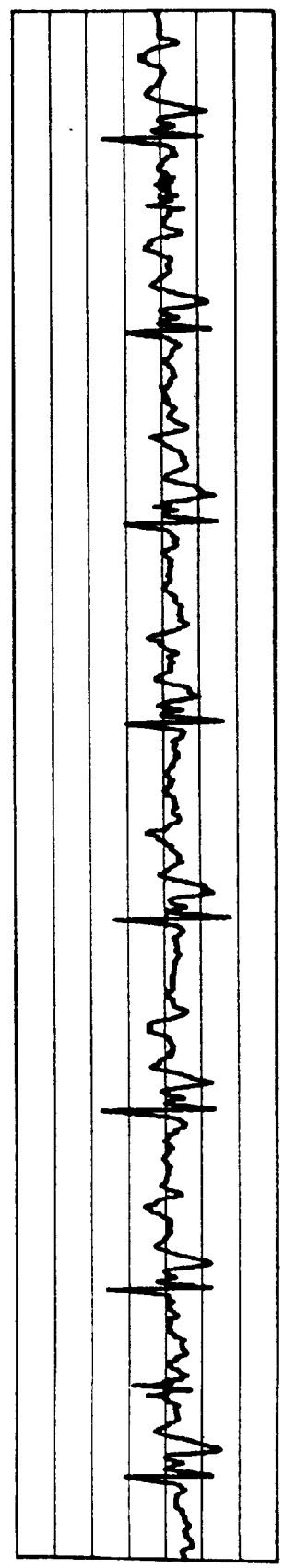

By way of comparison, electrocardiograms were measured using standard electrode arrays. One electrode was positioned on the sternum, at the level of the fifth intercostal space, and a central terminal was formed from three electrodes located on the left arm, right arm, and left leg. The potential between the chest electrode and the central terminal was recorded. The same electrodes from Quinton Instrument Company were used. FIG. 9a shows the electrocardiogram outside the magnet and FIG. 9b shows the electrocardiogram within a 0.5 T MRI magnet. FIG. 9c is an ECG of another individual outside a magnet and FIG. 9d is an ECG of the second individual within a 1.5 T magnet. The presence of the magnetic field distorts the ECG taken within the MRI magnet so that it cannot be used diagnostically.

The present invention should not be considered limited to the particular examples described above, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the instant specification. The claims are intended to cover such modifications and devices.

I claim:

1. An electrode assembly for monitoring bioelectric signals, the electrode assembly comprising:
   a first electrode member;
   a second electrode member that comprises two or more electrodes connected together by conductors, disposed around the first electrode member; and
   a first lead electrically connected to the first electrode member and a second lead electrically connected to the second electrode member, the first and second leads being adapted for coupling to a measurement device;
   whereby, when the electrode assembly is placed on a body of a person, a bioelectric signal is monitored by measuring the electrical potential between the first and second electrode members with the measurement device.

2. The electrode assembly of claim 1, wherein the first electrode member defines a simple closed curve.

3. The electrode assembly of claim 1, wherein the first electrode member comprises two or more electrodes connected together by conductors.

4. The electrode assembly of claim 1, wherein the first electrode member comprises three or more electrodes formed around the perimeter of a ring.

5. The electrode assembly of claim 4, wherein the three or more electrodes are spaced at regular intervals around the ring.

6. The electrode assembly of claim 1, wherein the first electrode member comprises three or more electrodes formed around the perimeter of a rectangle.

7. The electrode assembly of claim 1, wherein the first electrode member comprises a single electrode formed as a ring-like structure.

8. The electrode assembly of claim 1, wherein the first electrode member comprises one or more silver/silver chloride electrodes.

9. The electrode assembly of claim 1, wherein, when the electrode assembly is positioned on a patient, the electrode assembly is capable of monitoring electrical signals from the heart.

10. A device for monitoring bioelectric signals, comprising:
    a plurality of electrodes arranged in an array;
    a plurality of conductors connecting individual electrodes;
    two or more leads, each lead being coupled to either an electrode or a conductor, the leads being adapted for coupling to a measurement device; and
    a mechanism operatively connected to each of the electrodes to define two or more electrode members, each electrode member comprising two or more electrodes, one of the electrode members being disposed around the other electrode member, each of the electrode members being electrically coupled to at least one of the leads;
    whereby, when the electrode array is placed on a body of a person, a bioelectric signal is monitored by measuring the electrical potential between the leads coupled to the two electrode members.

11. The device of claim 10, wherein the mechanism is a switching mechanism which is configured and arranged to open or close electrical connections between the electrodes via the conductors.

12. The device of claim 10, wherein the mechanism is a software mechanism which defines the two or more electrode members by combining electrical measurements of two or more electrodes.

13. The device of claim 10, wherein the device further comprises a processor for operating the mechanism to sequentially form a series of pairs of the electrode members so that acceptable pairs of the electrode members can be determined for monitoring the bioelectric signals.

14. A method for monitoring bioelectric signals, the method comprising:
    positioning an electrode assembly on a body of a person, the electrode assembly comprising a first electrode member and a second electrode member, the second electrode member comprising two or more electrodes connected together by conductors, the second electrode member being disposed around the first electrode member; and
    measuring the potential between the first and second electrode members to monitor the bioelectric signal.

15. The method of claim 14, wherein the first electrode member comprises three or more electrodes connected by conductors.

16. The method of claim 14, wherein the second electrode member comprises three or more electrodes connected by conductors.

17. The method of claim 14, wherein the first electrode member comprises a single electrode formed in a ring.

18. The method of claim 14, wherein the method further comprises moving the electrode assembly one or more times to different positions on the patient and monitoring the bioelectric signal to determine which positions provide a predetermined signal quality.

19. The method of claim 14, wherein the method further comprises directing operation of an imaging apparatus in response to the monitored bioelectric signal.

20. A method for monitoring bioelectric signals, comprising:
    positioning an array of electrodes on a body of a patient, the array of electrodes comprising a plurality of electrodes forming the array; a plurality of conductors connecting individual electrodes; two or more leads, each lead being connected to either one of the electrode or one of the conductors, the leads being adapted for coupling to a measurement device; and a mechanism operatively connecting the electrodes for defining pairs of electrode members;

sequentially forming a series of pairs of electrode members using a switching mechanism, each electrode member comprising two or more electrodes, one of the electrode members being disposed around the other electrode member, and each of the electrode members being electrically coupled to one of the leads;

determining, for each pair of electrode members in the series, a quality characteristic of the bioelectric signal;

choosing one of the pairs based on the quality characteristic; and monitoring the bioelectric signal with the array configured as the chosen one of the pairs of electrode members, the bioelectric signal being measured as the potential between the leads attached to the electrode members.

21. The method of claim 20, wherein sequentially forming a series of pairs of electrode members comprises engaging a switching mechanism to close connections between electrodes forming the electrode members and to open connections between electrodes which do not form the electrode members.

22. The method of claim 21, wherein engaging the switching mechanism comprises operating the switching mechanism using signals from a processor coupled to the switching mechanism.

23. The method of claim 20, wherein the quality characteristic comprises at least one complete cycle of the bioelectric signal.

24. The method of claim 20, wherein the quality characteristic comprises a signal-to-noise ratio obtained from the electrode members.

25. The method of claim 20, wherein sequentially forming a series of pairs of electrode members comprises operating a software mechanism to form the electrode members by combining electrical measurements from two or more electrodes.

26. A method of monitoring a bioelectric signal, the method comprising:

positioning a first electrode array and a second electrode array on a patient, each of the first and second electrode arrays comprising a first electrode member and a second electrode member, the first electrode member comprising two or more electrodes connected together by conductors, the second electrode member being disposed around the first electrode member; and measuring the potential between the first and second electrode members of each of the first and second electrode arrays to monitor the bioelectric signal.

27. The method of claim 26, wherein positioning the first and second electrode arrays on a patient comprises positioning the first and second electrode arrays so that a first vector between the heart of the patient and the first electrode array is approximately orthogonal to a second vector between the heart of the patient and the second electrode array.

28. An electrode assembly for monitoring bioelectric signals, the electrode assembly comprising:

a first electrode member comprising two or more electrodes connected together by conductors;

a second electrode member disposed around the first electrode member; and a first lead electrically connected to the first electrode member and a second lead electrically connected to the second electrode member, the first and second leads being adapted for coupling to a measurement device;

whereby, when the electrode assembly is placed on a body of a person, a bioelectric signal is monitored by measuring the electrical potential between the first and second electrode members with the measurement device.

29. A method for monitoring bioelectric signals, the method comprising:

positioning an electrode assembly on a body of a person, the electrode assembly comprising a first electrode member and a second electrode member, the first electrode member comprising two or more electrodes connected together by conductors and being disposed around the first electrode member; and measuring the potential between the first and second electrode members to monitor the bioelectric signal.

30. A method of monitoring a bioelectric signal, the method comprising:

positioning a first electrode array and a second electrode array on a patient, each of the first and second electrode arrays comprising a first electrode member and a second electrode member, the first electrode member comprising two or more electrodes connected together by a conductor and being disposed around the first electrode member; and measuring the potential between the first and second electrode members of each of the first and second electrode arrays to monitor the bioelectric signal.

* * * * *